US012685852B2

(12) United States Patent
Kulik et al.

(10) Patent No.: US 12,685,852 B2
(45) Date of Patent: Jul. 21, 2026

(54) MICRONEEDLE ARRAY APPLICATOR

(71) Applicant: LTS Lohmann Therapie-Systeme AG, Andernach (DE)

(72) Inventors: Michael Kulik, Urmitz (DE); Thorsten Fehr, Andernach (DE); Stefan Erlhofer, Kempenich (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1249 days.

(21) Appl. No.: 17/423,408

(22) PCT Filed: Nov. 26, 2019

(86) PCT No.: PCT/EP2019/082533
§ 371 (c)(1),
(2) Date: Jul. 15, 2021

(87) PCT Pub. No.: WO2020/148008
PCT Pub. Date: Jul. 23, 2020

(65) Prior Publication Data
US 2022/0072290 A1 Mar. 10, 2022

(30) Foreign Application Priority Data

Jan. 17, 2019 (DE) .......................... 102019200557.8

(51) Int. Cl.
A61M 37/00 (2006.01)

(52) U.S. Cl.
CPC . A61M 37/0015 (2013.01); A61M 2037/0023 (2013.01); A61M 2037/0061 (2013.01)

(58) Field of Classification Search
CPC .. A61M 2037/0023; A61M 2037/0061; A61M 2037/0046; A61M 2037/003; A61M 37/0015
See application file for complete search history.

(56) References Cited

U.S. PATENT DOCUMENTS 6,780,171 B2 * 8/2004 Gabel ............... A61M 5/14248
604/181
8,758,298 B2 * 6/2014 Cantor .............. A61M 37/0015
604/117

(Continued)

FOREIGN PATENT DOCUMENTS

CN 1784248 A 6/2006
CN 101102720 A 1/2008
(Continued)

*Primary Examiner* — Bhisma Mehta
*Assistant Examiner* — Adam J. Cermak
(74) *Attorney, Agent, or Firm* — The Webb Law Firm

(57) ABSTRACT

An applicator the application of a microarray. The applicator includes a housing and a plunger that can move within the housing to accelerate the microarray. The applicator additionally includes a target force trigger, and the target force trigger secures the plunger in relation to the housing and releases the movement thereof when the target force is applied. The application system for application of a microarray, including such an applicator and a microarray or a microarray receiving portion, preferably connected to a microarray receiving portion cluster, having a microarray. The microarray or the microarray receiving portion are arranged relative to the applicator and/or connected to the applicator such that the plunger is able to apply the microarray.

17 Claims, 7 Drawing Sheets

(56) References Cited

U.S. PATENT DOCUMENTS

| | | | | |
|---|---|---|---|---|
| 9,131,954 | B2 | 9/2015 | Hong | |
| 9,687,640 | B2 | 6/2017 | Trautman et al. | |
| 10,245,422 | B2 | 4/2019 | Le et al. | |
| 10,300,260 | B2 | 5/2019 | Wirtanen et al. | |
| 11,420,812 | B2 * | 8/2022 | Sakazaki | A61M 37/0015 |
| 12,246,154 | B2 * | 3/2025 | Wirtanen | A61M 37/0015 |
| 2005/0165358 | A1 | 7/2005 | Yeshurun et al. | |
| 2007/0066935 | A1 | 3/2007 | Morishita et al. | |
| 2007/0293882 | A1 | 12/2007 | Harttig et al. | |
| 2008/0183144 | A1 * | 7/2008 | Trautman | A61M 37/0015 |
| | | | | 604/272 |
| 2009/0198189 | A1 * | 8/2009 | Simons | A61M 37/0015 |
| | | | | 604/173 |
| 2010/0222743 | A1 * | 9/2010 | Frederickson | A61M 5/158 |
| | | | | 604/173 |
| 2011/0276027 | A1 * | 11/2011 | Trautman | A61M 37/0015 |
| | | | | 604/173 |
| 2013/0006219 | A1 * | 1/2013 | Cantor | A61M 37/0015 |
| | | | | 604/173 |
| 2013/0023749 | A1 * | 1/2013 | Afanasewicz | A61B 5/6885 |
| | | | | 604/173 |
| 2013/0296824 | A1 * | 11/2013 | Mo | A61M 5/1454 |
| | | | | 604/173 |
| 2014/0257187 | A1 * | 9/2014 | Colburn | A61M 37/0015 |
| | | | | 604/173 |
| 2014/0276580 | A1 * | 9/2014 | Le | A61M 37/0015 |
| | | | | 604/173 |
| 2014/0336616 | A1 * | 11/2014 | Edwards | A61N 2/002 |
| | | | | 604/173 |
| 2015/0038897 | A1 * | 2/2015 | Daddona | A61M 37/0015 |
| | | | | 604/46 |
| 2015/0246214 | A1 * | 9/2015 | Simmers | A61M 37/0015 |
| | | | | 604/173 |
| 2015/0258319 | A1 * | 9/2015 | Simmers | A61M 37/0015 |
| | | | | 604/173 |
| 2015/0290444 | A1 * | 10/2015 | Wirtanen | A61M 37/0015 |
| | | | | 604/46 |
| 2016/0121092 | A1 * | 5/2016 | Kato | A61M 37/0015 |
| | | | | 604/173 |
| 2016/0158515 | A1 * | 6/2016 | Mohr | A61M 5/14593 |
| | | | | 604/173 |
| 2016/0339223 | A1 * | 11/2016 | Scherr | A61B 5/150282 |
| 2017/0120025 | A1 * | 5/2017 | Baker | A61M 37/0015 |
| 2017/0281852 | A1 * | 10/2017 | Bernstein | A61B 5/15188 |
| 2017/0281919 | A1 * | 10/2017 | Asai | A61M 37/0015 |
| 2018/0001071 | A1 | 1/2018 | Simmers | |
| 2018/0015271 | A1 * | 1/2018 | Junger | A61M 37/0015 |
| 2018/0099133 | A1 * | 4/2018 | Heuser | A61M 37/0015 |
| 2018/0304063 | A1 * | 10/2018 | Gonzalez | A61M 37/0015 |
| 2018/0326193 | A1 * | 11/2018 | Kobayashi | A61M 37/0015 |
| 2018/0361132 | A1 * | 12/2018 | Kobayashi | A61M 37/00 |
| 2020/0101205 | A1 * | 4/2020 | Todd | A61B 5/15113 |
| 2020/0101274 | A1 * | 4/2020 | Kobayashi | A61F 13/02 |
| 2020/0331691 | A1 * | 10/2020 | Sakazaki | B65D 85/24 |
| 2020/0368511 | A1 * | 11/2020 | Lemaire | B29C 45/561 |
| 2020/0391018 | A1 * | 12/2020 | Wirtanen | A61M 37/0015 |
| 2021/0178137 | A1 * | 6/2021 | Wirtanen | A61M 37/0015 |
| 2022/0072290 | A1 * | 3/2022 | Kulik | A61M 37/0015 |
| 2022/0072291 | A1 * | 3/2022 | Kulik | A61M 37/0015 |
| 2022/0072292 | A1 * | 3/2022 | Erlhofer | A61M 37/0015 |

FOREIGN PATENT DOCUMENTS

| | | | | |
|---|---|---|---|---|
| CN | 103179903 A | | 6/2013 | |
| JP | 2009240410 A | | 10/2009 | |
| TW | 1636805 B | * | 10/2018 | A61M 37/0015 |
| WO | WO-2008091602 A2 | * | 7/2008 | A61M 37/0015 |
| WO | 2016123665 A1 | | 8/2016 | |

* cited by examiner

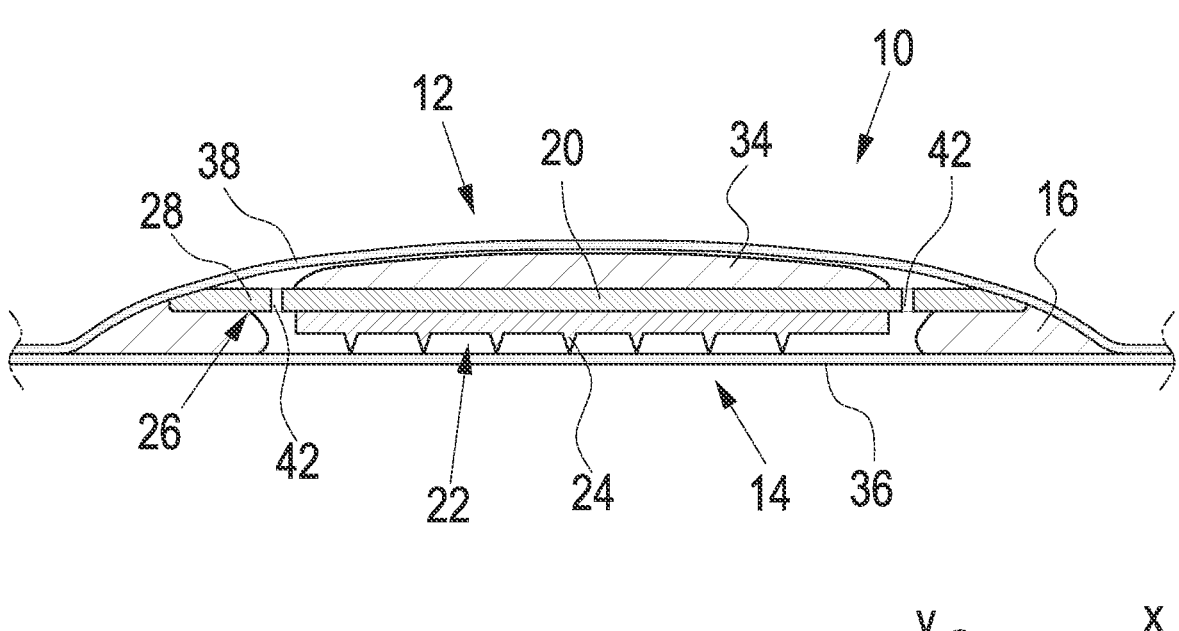
Fig. 5
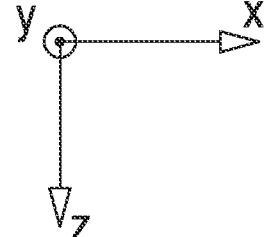

MICRONEEDLE ARRAY APPLICATOR

CROSS-REFERENCE TO RELATED APPLICATIONS

This application is the United States national phase of International Application No. PCT/EP2019/082533 filed Nov. 26, 2019, and claims priority to German Patent Application No. 102019200557.8 filed Jan. 17, 2019, the disclosures of which are hereby incorporated by reference in their entirety.

BACKGROUND OF THE DISCLOSURE

Field of the Disclosure

The disclosure relates to an applicator for the application of a microarray, as well as to an application system for the application of a microarray.

Description of Related Art

Microarrays comprise a plurality of microneedles which is usually arranged on a carrier element such as a patch, a plaster or the like, or is connected to a carrier element. Such microarrays comprise a large number of microneedles, e.g., 500-600 needles per cm². The needles are short in length so that upon pushing the microneedles into the skin of a patient, the needles will penetrate the skin of a patient only to an extent that nerves and blood vessels preferably do not come into contact with any needle tip. The microneedles include an active substance or a drug. The corresponding active substance may be applied on a surface of the needle or be provided in the needles. It is preferred that the needles are made of a material that dissolves in the skin of a patient.

When applying microarrays into human skin, there is a problem that the insertion of the microneedles into the skin must be reproducible so as to guarantee in particular a reliable drug delivery. Further, the insertion of the microneedles must be independent of the user or patient, since a reproducibility would otherwise not be guaranteed. In particular, the insertion of the microneedles should also be independent of the skin texture so that a certain penetration depth is guaranteed at all times.

In addition, microarray concepts and applicator concepts exist these days that are not compatible with each other. For example, some microarrays cannot be applied by a plurality of applicators.

SUMMARY OF THE DISCLOSURE

It is an object of the disclosure to provide an applicator for the application of a microarray, which improves the reproducibility of the insertion of the microarray. It is another object of the disclosure to provide an application system for the application of a microarray that allows for a simpler handling.

The applicator of the present disclosure is an applicator for the application of a microarray. Specifically, the application is a puncture, also referred to as the insertion of the microneedles of the microarrays, and/or a pressurization of the microarray, preferably for a long-term application. The microarray to be applied is, in particular, a part of a microarray receiving portion. The applicator comprises a preferably cylindrical housing. The cylindric shape of the housing is in particular a circular-cylindrical shape or a rectangular cylindrical shape, in particular a square cylindrical shape. A plunger is arranged movably in the housing. In the initial position the plunger is preferably fixed with respect to the housing, wherein this fixation is in particular configured to be releasable. The movability of the plunger within the housing serves to accelerate the microarray and/or to transmit force onto the microarray. The acceleration and/or the transmission of force serve to apply the microarray. Further, the applicator comprises a target force trigger. The target force trigger fixes the plunger relative to the housing, which fixation is released upon the application of a force to the target force trigger, which force at least corresponds to the target force, and thus, the plunger is released. Thus, the plunger is preferably movable relative to the housing after the application of at least the target force to the target force trigger. The target force trigger preferably is a structural element provided by structural design and/or a mechanical device. Specifically, the target force trigger may comprise a device which fails in a purposeful and predictable manner when a target force, in particular a defined target force, is applied.

In a preferred embodiment the target force at which the target force trigger operates, corresponds at least, in particular exactly, to an application force of the microarray. The application force preferably is the minimum necessary force, particularly preferred the optimal force for the application of the microarray. Preferably, it is an optimal puncturing force for the insertion of the microarray. In a preferred embodiment the target force trigger is thus configured such that the same releases the plunger when the optimal application force is applied. This results in the advantage that, on the one hand, the applicator releases the microarray for application when the target force is applied and that, on the other hand, this very target force at the same time serves to apply the microarray.

Advantageously, the applicator has an actuation surface for the application of the target force. The application of the target force refers in particular to the transmission or the effect of the target force for the actuation of the target force trigger. It is preferred that the actuation surface is accessible from the outside of the applicator. The actuation surface is actuatable in particular manually, e.g., by one or a plurality of a user's fingers and/or by means of a device. For example, a user may use a finger to press on the actuation surface and thereby exert a force. Preferably, the actuation surface is connected with the plunger, wherein in particular an integral connection, or a connection that may be referred to as being integral, is preferred. Accordingly, the actuation surface may in particular be a part of the plunger. Specifically, the actuation surface is located on the side opposite the side of the plunger that acts on the microarray for the application thereof.

It is preferred that the plunger-like structure is prestressed, in particular in the initial position. Thereby, preferably after the release of the plunger by the target force trigger, the plunger is moved automatically, in particular without any external influence, due to the prestress. In particular, the prestress is such that it causes a movement of the plunger so that an application is effected, preferably with an optimal application force. The prestress is applied indirectly or directly to the plunger. The applicator preferably comprises a prestressing device for the generation of the prestress. The prestressing device is provided in particular between the housing and the plunger. It is also possible that the prestressing device is connected, in particular integrally, with the plunger. Preferably, the prestressing device comprises a spring sheet, in particular analogous to the design of a "clicker". In the embodiment using a spring sheet it is preferred that the plunger comprises the spring sheet, in particular that the plunger is connected, preferably integrally, with the spring sheet. As an alternative or in addition, it is possible that the prestress exists due to an internal material stress, in particular due to an internal material stress of the plunger. The internal material stress is effected preferably by a material pairing. Here, it is possible that the prestressing device comprises a bimetal. Preferably, the material pairing is obtained through two, in particular plate-shaped materials which are preferably connected with each other using an adhesive and/or a soldered connection. Here, it is particularly preferred that one or both materials show a prestress, in particular a bend. In addition, it is preferably possible that the material stress prevails due to a frozen internal stress caused in the context of an injection molding manufacturing process. Using frozen internal stress, it is in particular possible to use only a single material. It is possible that the prestressing device comprises a spring device, in particular a spring, for the generation of the prestress. It is also possible that the prestress is effected by means of thermal stress, in particular thermal stress in the prestressing device and/or in the plunger.

In a preferred embodiment the plunger-type is at least substantially rigid. It is possible in particular that the plunger has a rigid base body and additional flexible elements such as, e.g., a preferably outer bead and/or groove. The bead and/or the groove are preferably flexible. The rigid design of the plunger is in particular stiff and/or inflexible. The rigid design has an advantage over non-rigid designs in that a more precise and thus reproducible target force triggering can be realized.

In particular, the plunger comprises a convex structure which is connected, in particular integrally, with the same. The convex structure is preferably located on the side of the plunger that is configured to act on the microarray. Using the convex structure, it is advantageously possible to transmit a punctual force in particular onto the microarray to be applied.

In a preferred embodiment the target force trigger has a rated breaking point and/or a fit. The fit comprises in particular a bead and/or a groove, wherein the groove and/or the bead are preferably flexible. In particular, the rated breaking point and/or the fit is arranged between the housing and the plunger. Thus, preferably the housing comprises a first part of the rated breaking point and/or the fit, e.g., the bead or the groove, and the plunger comprises a second part of a rated breaking point and/or a fit, e.g., a bead or a groove.

Instead of or in addition to the rated breaking point and/or the fit, it is preferably also possible that the target force trigger comprises a clamping and/or a spring-loaded retaining device which acts in particular on the plunger.

In a preferred embodiment the applicator comprises a hinge device, in particular for a defined mobility of the plunger relative to the housing. In particular, the hinge device is a flexure hinge.

The hinge device preferably comprises a sliding joint and/or a helical joint and/or a revolute joint and/or a ball joint. The sliding joint is an in particular cylindrical slideway, for example. The cylindrical shape is preferably a circular-cylindrical shape or a cuboid-cylindrical shape, in particular a square shape. This slideway is provided in particular inside the housing so that the plunger can slide in this slideway. The revolute joint is preferably an articulated joint or a hinge. It is preferred that the revolute joint and/or the ball joint are provided on one side of the housing.

In particular, it is possible that the hinge device causes a prestressing of the plunger. Here, it is preferred that the hinge device comprises the prestressing device and/or an internal material stress.

It is preferred that the applicator has a retaining device for the fixation of the plunger. This fixation of the plunger by means of a retaining device is effected in particular after the movement release of the plunger by the target force trigger. Preferably, the retaining device fixes the plunger in a deflected position, in particular a fully deflected position. The fully deflected position corresponds in particular to the position of the microarray in the applied state. The retaining device preferably is a latching device, in particular a snap-in hinge and/or snap lock. As an alternative or in addition, a groove and/or a bead as a retaining device are also possible, wherein the groove and/or bead are preferably flexible.

In particular, the microarray is indirectly or directly connected with the plunge-type element. Preferably, the microarray is connected, in particular by adhesion, with the plunger, for example by means of the microarray's patch. On the other hand, it is possible that the plunger comes into contact with the microarray only due to its movement.

In a preferred embodiment the applicator comprises a connection device for the connection of the applicator with a microarray receiving portion and/or an application site. The application site is preferably the skin of a person. The microarray receiving portion in particular is a microarray receiving portion to be described in the following.

The connection device comprises in particular a thread and/or a plug-in connection and/or a form-fitting connection element and/or a flange and/or a bayonet lock connection element and/or a magnetic connection element, in particular a magnet, and/or an adhesive connection device and/or a lug and/or a loop. If the connection device is embodied as a thread and/or a plug-in connection and/or a form-fitting connection element and/or a flange and/or a bayonet lock connection element and/or a magnetic connection element, it is preferred that the same are configured such that they can cooperate with a corresponding mating part of the microarray receiving portion and thus establish a connection. If embodied as an adhesive connection device, it is preferred that an adhesive connection of the applicator with the microarray receiving portion and/or the application site can be made. If embodied as a lug and/or a loop, it is preferred that the lug and/or the loop can be placed around a part of the body, e.g., an arm of a patient, and that a connection or a fastening of the applicator, preferably with the microarray connected thereto, to an application site can be made in this manner.

The application system of the present disclosure for the application of a microarray comprises an applicator as described above. In addition, the application system comprises a microarray and/or a microarray receiving portion with a microarray, the microarray receiving portion preferably being connected with a microarray receiving portion cluster. The microarray or the microarray receiving portion are arranged relative to the applicator and/or connected with the applicator such that the plunger can apply the microarray. If the application system comprises a microarray receiving portion which is connected with a microarray receiving portion cluster, preferably is a part of the microarray receiving portion cluster, the applicator is preferably only connected with this single microarray receiving portion of the microarray receiving portion cluster and/or is arranged correspondingly. The applicator system of the present disclosure results in the advantage that the applicator and the microarray are matched, so that it is possible to realize a platform concept, for example.

In a preferred embodiment the microarray receiving portion is a microarray receiving portion for storing a microarray and/or for handling a microarray and/or for guiding a microarray during application. The microarray receiving portion preferably comprises a first side, wherein the first side preferably is the upper side of the microarray receiving portion. The first side is in particular the side averted from the application site, especially the skin. In addition, the microarray receiving portion preferably comprises a second side, preferably a lower side, wherein this second side preferably is the side facing toward the skin. The microarray receiving portion preferably comprises a carrier structure which is configured to be connected with the application site. It is particularly preferred that the application site is the skin of a user. The carrier structure thus preferably comprises the contact surface of the microarray receiving portion with the skin. This contact surface may in particular be adhesive. Thus, the microarray receiving portion can be adhered to the skin by the contact surface of the carrier structure. Furthermore, the microarray receiving portion preferably comprises a carrier surface connected with the carrier structure. In a preferred embodiment this carrier surface is formed as an in particular round or rectangular plate. It is preferred to realize the carrier surface with a substantially two-dimensional surface. Preferably, the microarray is connected with the carrier surface. The connection between the microarray and the carrier surface may be made in particular such that a patch of the microarray is glued and/or welded to the carrier surface. On the other hand, a design is also possible in which the microarray is formed as a single piece, also referred to as being integral, with the carrier surface. It is possible that the microstructures, preferably the microneedles of the microarray, are mounted directly on the carrier surface. It is preferred that the carrier structure is designed and/or connected with the carrier surface such that in the initial state the carrier surface and the microarray are spaced from the application site. The carrier surface may be designed such that it constitutes a sterile barrier especially toward the first side. Further, the microarray receiving portion preferably comprises a hinge device, referred to as a microarray receiving portion hinge device, between the carrier surface and the carrier structure. The a microarray receiving portion hinge device is preferably designed such that it allows for a movement of the microarray, which is connected with the carrier surface, relative to the carrier structure. This relative movement of the microarray relative to the carrier structure is effected in particular such that the movement is performed along the extension of the microstructures, preferably the microneedles, of the microarray. In other words: the microarray is preferably connected with the carrier structure in a supported manner on the carrier surface via the microarray receiving portion hinge device such that in particular the spacing of the microarrays from the skin is overcome by the movement and thus an application of the microarray into the skin is performed. Here, the microarray receiving portion hinge device is configured in particular such that it only allows a movement along the extension of the microstructures. However, a design is also possible in which additional movements, such as in particular a tilting or a transversal movement, are possible. The microarray receiving portion hinge device may be configured such that it only allows a movement to one side, in particular towards the skin. On the other hand, the microarray receiving portion hinge device may also be configured such that it allows a movement to both sides, in particular a back and forth movement. The carrier structure preferably forms a, in particular, cylindrical housing of the microarray receiving portion. The cylindrical shape of the housing may preferably be a circular or rectangular, in particular square, or oval base.

In a preferred embodiment the microarray receiving portion hinge device comprises at least a first flexure hinge, referred to as the first microarray receiving portion flexure hinge. Preferably, the first microarray receiving portion flexure hinge is formed integrally with the carrier surface. In case of an integral configuration consisting of the microarray receiving portion flexure hinge and the carrier surface, it is in particular possible that the microarray is not directly connected with the microarray receiving portion flexure hinge. Here, an integral configuration of the microarray and the microarray receiving portion flexure hinge is also possible.

Preferably, besides the first microarray receiving portion flexure hinge, the microarray receiving portion hinge device comprises a second flexure hinge, referred to as a second microarray receiving portion flexure hinge. Here, it is preferred that the first microarray receiving portion flexure hinge and the second microarray receiving portion flexure hinge are arranged substantially parallel to each other. The second microarray receiving portion flexure hinge forms in particular an action surface for preferably external actions on the microarray receiving portion. In particular, the second microarray receiving portion flexure hinge may be configured such that it can be moved from outside. It is preferred that the second microarray receiving portion flexure hinge thus moved can act upon the first microarray receiving portion flexure hinge. Both microarray receiving portion flexure hinges are configured or arranged in particular such that the microarray and/or the carrier surface can only experience a one-dimensional, preferably linear deflection. Preferably, this deflection is a deflection along the extension of the microstructures of the microarray.

In a preferred embodiment the microarray receiving portion comprises a blocking device for the fixation of the first microarray receiving portion flexure hinge and the second microarray receiving portion flexure hinge relative to each other. In particular, the blocking device is a latching device which, upon latching, prevents a relative movement of the first microarray receiving portion flexure hinge to the second microarray receiving portion flexure hinge. Preferably, the latching device is a latching pin between the first microarray receiving portion flexure hinge and the second microarray receiving portion flexure hinge. The latching pin may be designed such that it is connected with the first or the second microarray receiving portion flexure hinge already in the initial state and, upon latching, locks in with the respective other microarray receiving portion flexure hinge and thus prevents a relative movement of the two microarray receiving portion flexure hinges. On the other hand, it is also possible that, upon latching, the latching pin locks in with both microarray receiving portion flexure hinges.

The first microarray receiving portion flexure hinge and/or the second microarray receiving portion flexure hinge are in particular linear microarray receiving portion flexure hinges. It is particularly preferred that these are linear plate-shaped flexure hinges. A linear plate-shaped flexure hinge is a rigid plate with at least two portions connected by webs for relative movement with respect to each other. The mobility of the portions relative to each other is restricted in particular to parallel and/or rectangular movements. The webs and/or the portions are made in particular by punching and/or laser cutting a rigid plate. A linear plate-shaped flexure hinge is also referred to as a diaphragm flexure hinge. It is preferred that the carrier surface is formed integrally with the microarray receiving portion hinge device and/or the microarray. It is also possible that the carrier surface is integrally connected with the support structure.

In a preferred embodiment the microarray receiving portion flexure hinge device has a degree of freedom of 1. Preferably, the microarray receiving portion hinge device thus only allows for linear deflections, in particular along the extension of the microstructures of the microarray. In other words, the microarray receiving portion hinge device is preferably configured such that it only allows for movements along the Z-direction. It is particularly preferred that the microarray receiving portion hinge device only allows for movements in one direction, preferably in the direction of the needle tips of the microneedles.

On the one hand, it is possible that the microarray receiving portion hinge device is configured such that it automatically restores the carrier surface to the initial position after a deflection. On the other hand, it is possible that the microarray receiving portion hinge device maintains the carrier surface in a deflected position. Thus, according to the first possible configuration, in particular upon an insertion of the microneedles into the skin, the microneedles are subsequently pulled out of the skin as soon as the microarray receiving portion hinge device is no longer deflected, in particular from outside. According to the possible second configuration it is possible, in particular, that after a first deflection of the microarray receiving portion hinge device, the microneedles penetrate the skin and are deflected preferably by the microarray receiving portion hinge device and are thus maintained in a state penetrating the skin. Here, it is preferred That the microarray receiving portion comprises a fixation device, in particular a latching fixation device, wherein the fixation device blocks or fixes the microarray receiving portion hinge device and/or the carrier surface in the deflected position and thereby prevents a restoring of the microarray to the initial position, at least temporarily. In particular, the latching fixation device is a snap-in hinge comprising the microarray receiving portion hinge device and/or a snap lock actin in particular between the carrier surface and the carrier structure It is preferred that the microarray receiving portion, in particular the microarray receiving portion hinge device, comprises a prestressing device such as a spring. The prestressing device is configured in particular such that it causes an acceleration of the carrier surface during deflection and/or a maintaining of the carrier surface in the deflected position.

It is preferred that the microarray receiving portion comprises a force induction structure connected with the rear side of the microarray. In particular, the force induction structure may be connected with the carrier surface opposite the microarray. It is preferred that the force induction structure is of a convex design.

It is preferred that the microarray receiving portion and the applicator are arranged relative to each other and/or are connected with each other such that the plunger of the applicator acts indirectly or directly on the microarray of the microarray receiving portion. When the plunger acts on the microarray of the microarray receiving portion, in particular, an indirect or immediate connection and/or an indirect or direct impact of the plunger and the microarray is effected, preferably during the movement of the plunger. When the plunger acts indirectly on the microarray, the microarray receiving portion and the applicator are preferably arranged and/or connected such that the plunger acts, in particular strikes, indirectly on the force induction structure or the carrier surface or the microarray receiving portion flexure hinge or the second microarray receiving portion flexure hinge.

The microarray receiving portion in particular comprises a bottom film. The bottom film is preferably arranged on the second side of the microarray receiving portion. In a preferred embodiment the bottom film forms a sterile barrier of the microarray on the second side towards the environment. It is possible that the bottom film is designed such that it can be penetrated by the microarray. Thus, in particular microneedles of the microarray can penetrate the bottom film.

It is preferred that the bottom film is connected with the carrier structure. Here, it is particularly preferred that the bottom film is connected with the carrier structure such that it can be peeled off or removed. This peel-off connection is achieved in particular by adhering the bottom film to the carrier structure. Thus, it is possible that, in particular prior to use, a user removes the bottom film from the carrier structure and thereby releases the microarray.

It is possible that the bottom film comprises an adhesive layer. Thus, it is in particular possible to fasten the microarray receiving portion on an application site.

The microarray receiving portion preferably comprises a cover film. The cover film is connected in particular with the carrier structure. Here, a permanent, non-detachable connection is preferred. In particular, the cover film may be welded, in particular by ultrasound welding, or adhered to the carrier structure. The cover film preferably forms a sterile barrier on the first side of the microarray receiving portion towards the environment.

The cover film is in particularly formed to be flexible and/or fragile. With a flexible design, the cover film can in particular be acted upon from outside, so that the cover film yields flexibly. With a fragile, preferably perforated design, the cover film microarray break when acted upon from outside and may thus allow to act on the microarray receiving portion from outside.

In a preferred configuration the microarray receiving portion comprises a connection device, referred to as a microarray receiving portion connection device. The microarray receiving portion connection device is provided in particular on the first side of the microarray receiving portion. It is particularly preferred that the microarray receiving portion connection device is connected, preferably integrally, with the carrier structure. The microarray receiving portion connection device in particular is a microarray receiving portion connection device for connection with the applicator for the application of a microarray. The microarray receiving portion connection device preferably comprises a thread and/or a plug-in connector and/or a form-fitting connection element and/or an adhesive spot and/or a flange. Preferably, the microarray receiving portion connection device one such above-mentioned connection element that corresponds to a mating part of the connection device of the applicator. Using the microarray receiving portion connection device, preferably the applicator can be connected with the microarray receiving portion.

The microarray receiving portion cluster preferably comprises a plurality of microarray receiving portions according to the above definition. The plurality of microarray receiving portions may comprise identical or different microarrays so that in particular different microarray receiving portions with different active substances and/or different needle numbers etc. may be provided. The carrier surfaces and/or the bottom films and/or the cover films and/or the carrier structures of the plurality of microarray receiving portions are preferably connected with each other, wherein in particular an integral connection is preferred. Thus, a plurality of microarray receiving portions can be connected with each other. In particular, it is thus possible to produce a plurality of microarray receiving portions together, preferably continuously. It is also possible, advantageously, to jointly place a plurality of connected microarray receiving portions on a body site, in particular on a curved skin zone, provided for application. This plurality of microarray receiving portions may then be applied simultaneously or temporally offset. Preferably, the applicator can be used to apply the microarray receiving portions of the microarray receiving portion cluster, wherein it is preferred in particular to apply the microarray receiving portions individually one after the other.

The disclosure will be described hereinafter with reference to preferred embodiments and to the drawing.

BRIEF DESCRIPTION OF THE DRAWINGS

In the Figures:

FIG. 5 is a schematic sectional view of an embodiment of a microarray receiving portion, wherein the microarray receiving portion essentially corresponds to the microarray receiving portion of FIG. 4 along the section plane V.

DETAILED DESCRIPTION

Figure 1A:
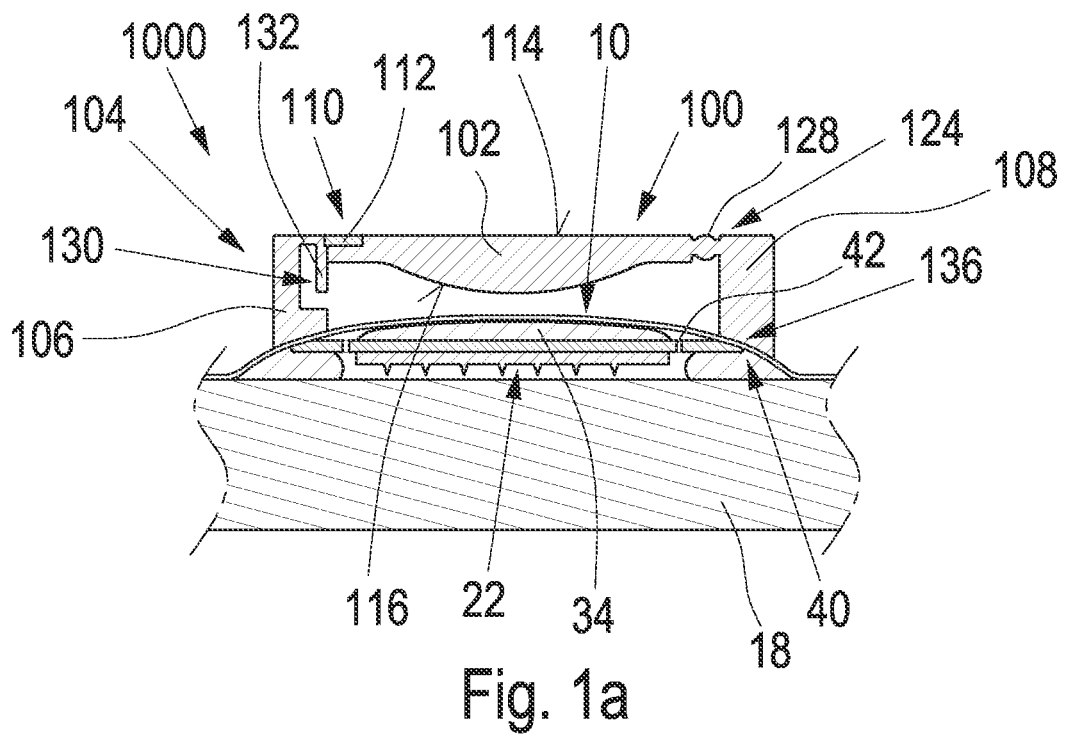
FIG. 1a is a schematic sectional view of an embodiment of an application system according to the present disclosure comprising an embodiment of an applicator according to the present disclosure, as well as an embodiment of a microarray receiving portion in an initial position.

Similar or identical components or elements are identified by the same reference numerals in the Figures. Specifically for the purpose of increased clarity, preferably already identified elements are not provided with reference numerals in all Figures.

FIG. 1a is a schematic sectional view of an embodiment of an application system 1000 according to the present disclosure comprising an embodiment of an applicator 100 according to the present disclosure, wherein the applicator 100 is connected with an embodiment of the microarray receiving portion 10. The microarray receiving portion 10 corresponds to the microarray receiving portion 10 of FIG. 5, described in more detail below.

The microarray receiving portion 10 is arranged on an application site 18, the application site 18 being in particular the skin of a user or a patient. For application, a bottom film 36 (see FIG. 5 and the corresponding description) has been peeled off or removed.

The essentially cuboid applicator 100 is set on the microarray receiving portion 10 or is connected to the microarray receiving portion 10. Besides the cuboid shape, which may, e.g., be square or rectangular, other shapes are possible, e.g., a circular cylindrical shape etc. The connection of the applicator 100 with the microarray receiving portion 10 is made in particular by means of the connection device 136 of the applicator 10, as well as the microarray receiving portion connection device 40 of the microarray receiving portion 10. On the one hand, this connection can be made by setting the applicator 100 on the microarray receiving portion 10, preferably in a loose manner. On the other hand, the connection between the connection device 136 of the applicator 100 and the microarray receiving portion connection device 40 can be realized by means of a structural connection. In the context of the structural connection, it is preferred that the connection device 136 of the applicator 100 comprises a thread and/or a plug-in connection and/or a form-fitting connection element and/or a flange and/or an adhesive connection device. The microarray receiving portion connection device 40 thus preferably comprises a corresponding mating part. Further, it is possible as an alternative or in addition that the connection device 136 of the applicator 100 comprises a connection element such as in particular a lug and/or a loop, wherein the applicator 100 is connected, e.g., with a body part, such as an arm. In particular, it is possible that a loop of the connection device 136 of the applicator 100 is placed around an arm, preferably under tension, and the applicator is thus attached on the skin of a user, preferably with the microarray receiving portion 10 below the applicator.

The applicator 100 comprises a preferably cuboid housing 104. The outer wall 106 and the outer wall 108 of the housing are illustrated. Preferably, the housing further comprises two further side walls which correspond to the front and rear sides. On one side (the top in the Fig.), the housing 104 ends in an actuation surface 114 of the plunger 102. The plunger 102 is connected with the side wall 108 through a hinge device 124. In the embodiment illustrated, the hinge device 124 comprises a revolute hinge 128, which preferably is a flexure hinge. On the opposite side, the plunger 102 is connected with the outer wall 106 through a target force trigger which, as illustrated, has a rated breaking point 112.

The actuation surface 114 can be operated from outside so that, e.g., a user can press on the actuation surface 114 with his finger.

The plunger 102 may have a first side and a second side opposite the first side. Located opposite or oriented opposite the actuation surface 114, the plunger 102 has a convex structure 116. The actuation surface 114 may be connected with the first side of the plunger 102. The convex structure 116 may be connected with the second side of the plunger 102. This convex structure 116 is located opposite the convex force induction structure 34 of the microarray receiving portion 10.

Figure 1B:
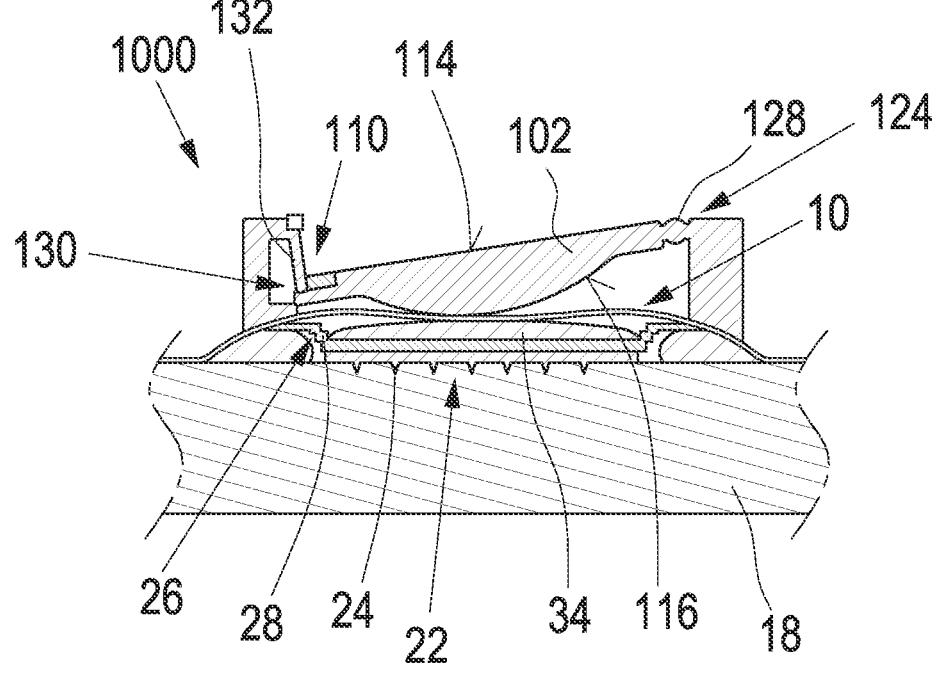
FIG. 1b is a schematic sectional view of the application system of FIG. 1a in a position for application.

FIG. 1b illustrates the applicator in a triggered or applied position.

For example, due to the pressure exerted by a user with his finger on the actuation surface 114, the rated breaking point 112 has been ruptured, effecting a deflection of the plunger 102 around the hinge device 124.

Due to the deflection of the plunger 102 an action occurs, e.g., a force transmission from the convex structure 116 of the plunger-type structure 102 onto the convex force induction structure 34 of the microarray receiving portion 10. Due to the two contacting convex structures 116, 34, the force transmission is effected as a punctual force, whereby a deflection of the microarray 22 in a perpendicular direction or along the normal vector to the application site 18. The microarray 22 is deflected along the microarray receiving portion hinge device 26.

The deflection of the microarray 22 causes a piercing of the microneedles 24 into the application site 18. It is preferred that the target force trigger 110, i.e., the rated breaking point 112 in the Fig., is designed such that the target force causing a triggering of the target force trigger 110 corresponds to a required, in particular optimal application force of the microarray 22. Accordingly, as soon as a target force is applied to the target force applicator 110 via the actuation surface 114, an optimal application of the microarray 22 is effected.

In a deflected position, the plunger 102 is retained or fixed by the retaining device 130 so that the plunger 102 is pressed further on the microarray 22. In this manner, an application of the microneedles 24 of the microarray 22 is effected over a longer period. As illustrated, the retaining device 130 comprises a kind of inner wall which is flexible and is prestressed towards the center of the housing. When the plunger 102 passes the inner wall 132 vertically, the inner wall 132 is deflected towards the center of the housing and thereby the plunger 102 and the inner wall 132 are canted, as it were, whereby the plunger-like element is fixed in the deflected position.

Figure 2A:
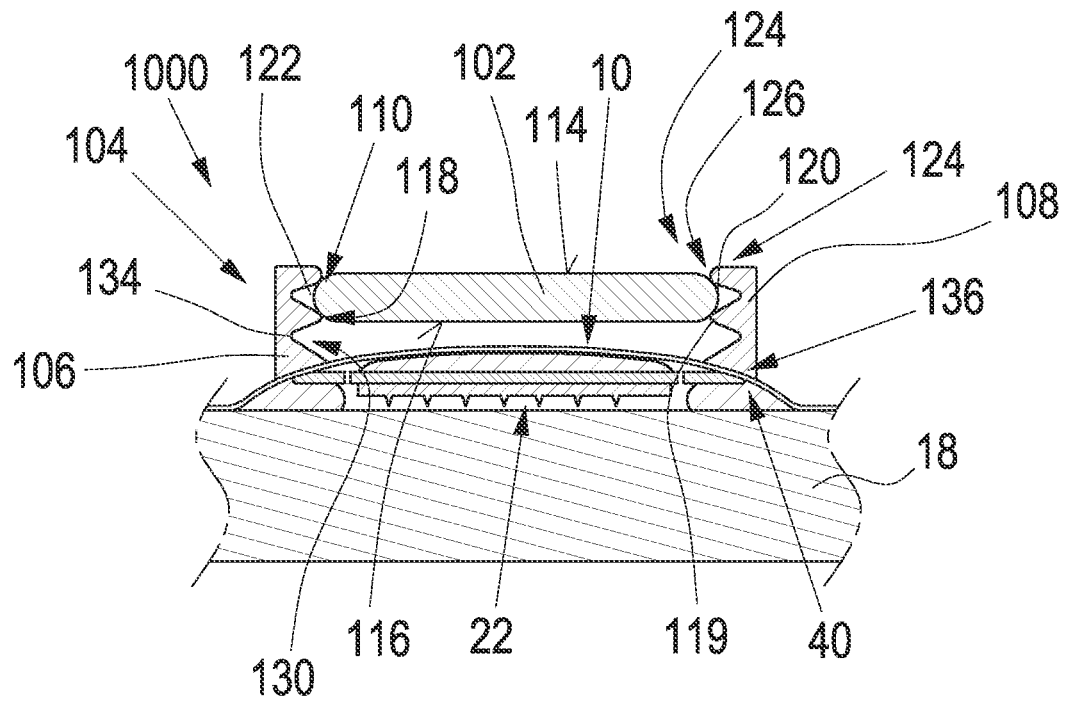
FIG. 2a is a schematic sectional section of another embodiment of an application system of the preset disclosure comprising another embodiment of an applicator according to the present disclosure, as well as another embodiment of a microarray receiving portion in an initial position.

FIG. 2a illustrates another embodiment of an application system 1000 of the preset disclosure comprising another embodiment of an applicator 100 according to the present disclosure, wherein the microarray receiving portion 10 essentially corresponds to the microarray receiving portion 10 of FIG. 1a.

Similar to the embodiment of FIG. 1a, the applicator 100 is connected with the microarray receiving portion 10 through the connection device 136, as well as the microarray receiving portion connection device 40.

In the embodiment illustrated, the target force trigger 110 is designed as a fit 118 between the plunger 102 and the housing 104. For this purpose, the plunger-like element 102 comprises at least one flexible bead 120. In the initial position illustrated in FIG. 2b, this bead 120 is located in a groove 122. The bead 120 and/or the groove 122 are preferably flexible. This flexible design is in particular configured such that a fit force to be overcome is defined thereby. This fit force corresponds to the target force of the target force trigger 110.

Figure 2B:
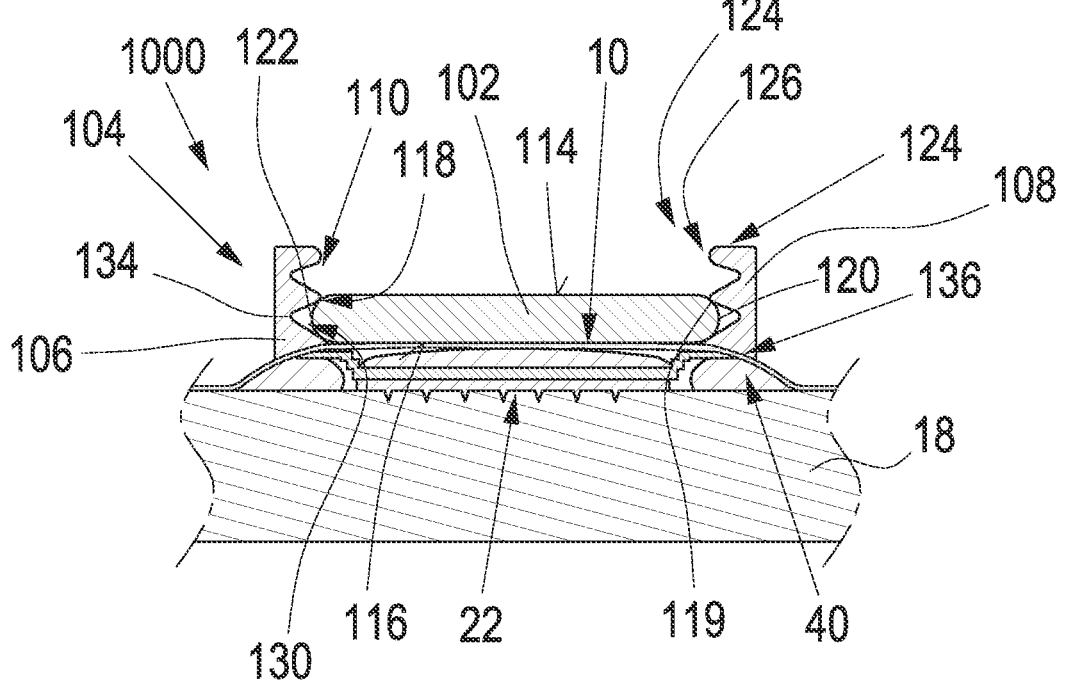
FIG. 2b is a schematic sectional view of the application system, of FIG. 2a in a position for application.

For example, a user pressing on the actuation surface 114 with the target force, causes the bead 120 and/or the protrusion 119 of the groove 122 to be displaced, so that a vertical (downward) movement of the plunger 102 is effected (see FIG. 2b). The movement of the plunger 102 relative to the housing 104 occurs along the hinge device 124, which is illustrated as a sliding joint 126. The sliding joint 126 is defined by the inner hollow shape of the housing 104, so that the plunger 102 can move vertically, preferably with a degree of freedom of 1, inside the housing, i.e., the sliding joint 126.

The applicator 100 comprises a retaining device 130 configured as a further groove 134. After a vertical displacement of the plunger 102 (see FIG. 2b), the plunger 102 remains in the retaining device 130, preferably by a type of latching or snapping-in. Thereby, the plunger 102 is pressed further onto the microarray of the microarray receiving portion 10 (see FIG. 2b).

In the embodiment illustrated, the housing 104 is cuboid in shape, however, a circular-cylindrical design is also possible. In addition, instead of the combinations of a bead 120 and a groove 122 of the target force trigger 110, as illustrated, it is possible to provide only a bead 120 or a groove 122. Furthermore, it is possible that only the plunger 102 has a bead or a groove or that only the housing has a bead or a groove. This applies analogously to the retaining device 130.

Figures 3, 4:
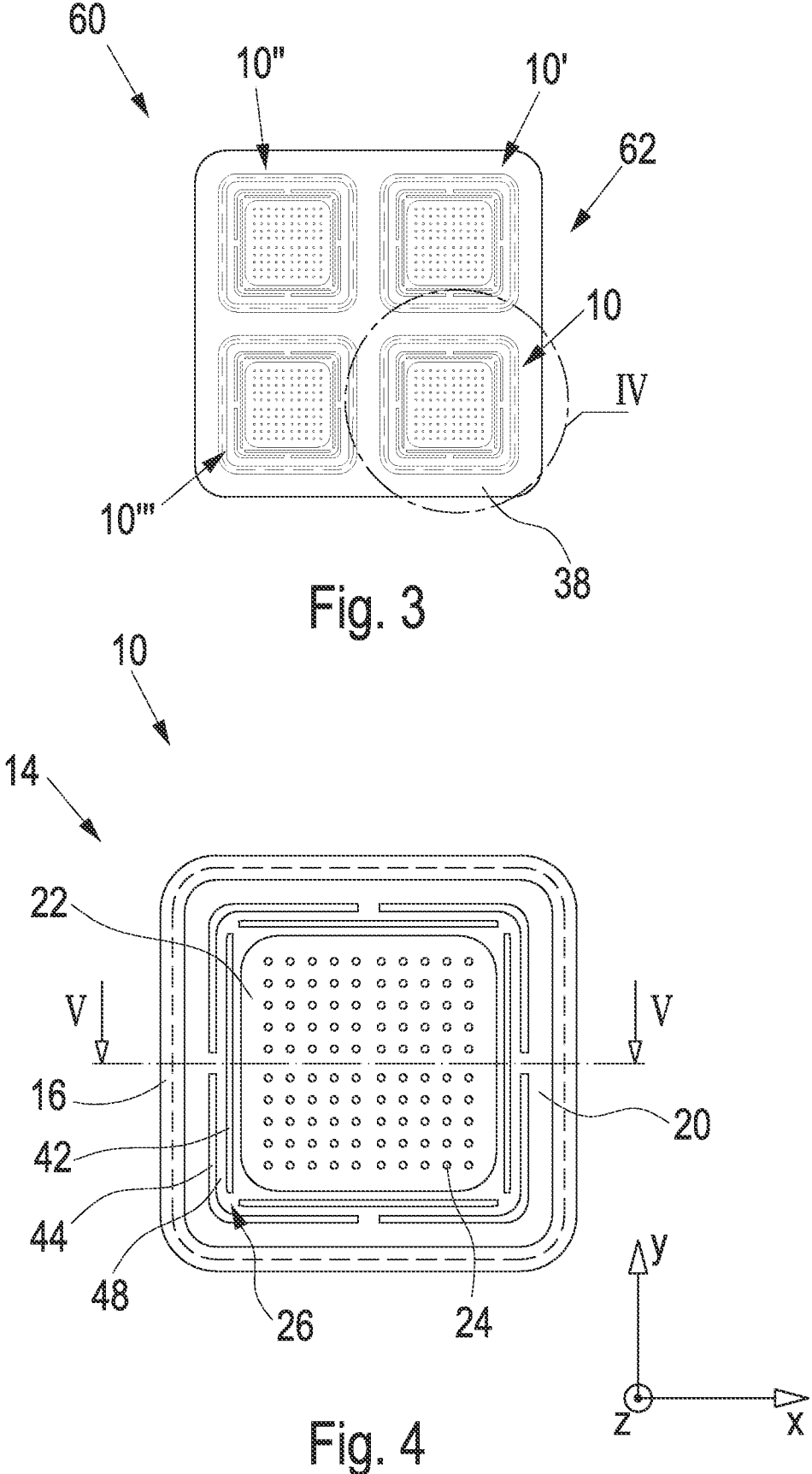
FIG. 3 is a schematic top plan view of an embodiment of a microarray receiving portion cluster.
FIG. 4 is a detail of the region IV in FIG. 3, illustrating an embodiment of a microarray receiving portion.

FIG. 3 is a top plan view of the lower side of an embodiment of a microarray receiving portion cluster 60 (with the bottom film 36 omitted).

The microarray receiving portion cluster 60 shows a plurality of embodiments of microarray receiving portions 10, 10', 10", 10''', which are connected with each other through a cover film 38. For applying the microarray receiving portion cluster 60, the same is placed in particular on human skin, so that the side 62 of the microarray receiving portion cluster 60 illustrated rests on the skin and is thus shielded from the environment by the cover film 38. Here, the cover film 38 and/or the microarray receiving portions 10, 10', 10", 10''' are preferably flexible, so that the microarray receiving portion cluster 60 in particular clings to a curved skin zone. After the microarray receiving portion cluster 60 has been placed on the skin, it is possible to apply in particular individual microarray receiving portions 10 independently, or it is possible to apply all microarray receiving portions together.

Instead of the embodiment illustrated, it is possible that the carrier structures 16 are connected, in particular integrally, with each other.

FIG. 4 is a detail of the microarray receiving portion 10 of FIG. 3. FIG. 4 illustrates the lower side 14 of the microarray receiving portion 10 which is opposite the upper side 12 not illustrated.

The microarray receiving portion 10 comprises a circumferential carrier structure 16 which in part protrudes beyond a carrier surface 20, wherein the carrier structure 16 is connected with the carrier surface 20 by the portion overlapping the carrier surface (see FIG. 5). Preferably, the protruding portion of the carrier structure 16 is connected with the cover film 38 not illustrated in FIG. 4 (see FIGS. 3 and 5). The connection between the cover film 36 and the carrier structure 16 is preferably made by welding and/or gluing, wherein, however, an integral or another design is possible. The connection between the carrier structure 16 and the carrier surface 20 may be made in particular by gluing and/or welding, but may also be formed as an integral connection. The carrier surface 20 is connected with a microarray 22 having a plurality of microneedles 24. As illustrated, the microarray 22 is a patch with microneedles 24 arranged thereon, in particular formed integrally therewith. Here, the microneedles 24 preferably extend in a cone shape from the image plane (in Z-direction). Instead of the design illustrated, it is also possible to connect the microarray 22 directly with the carrier surface 20, wherein an integral connection is possible as well. Accordingly, it is possible to design the carrier surface 20 integrally with the microarray 22 and/or the microneedles. The carrier structure 16 preferably has a height (protruding from the image plane in the Fig.) which in particular provides for a spacing of the carrier surface 20 from an application site.

The microarray receiving portion 10 of FIG. 4 further comprises a microarray receiving portion hinge device 26. Here, the microarray receiving portion hinge device 26 is designed as a microarray receiving portion flexure hinge, in particular a linear plate-shaped flexure hinge. To this end, the carrier structure 16 has slots 42, 44 which are formed in particular by punching a plate which preferably corresponds substantially to the carrier surface 20. Webs 48 are located between these slots 42, 44. These preferably flexible webs 48 allow for a mobility of the inner portion of the carrier surface 20 relative to the outer portion. The microarray receiving portion hinge device 26 in particular allows for a movement of the microarray in the Z-direction. However, due to the design of the embodiment of the microarray receiving portion hinge device 26 illustrated, a tilting of the microarray 22 is also possible, so that a movement around the X- and/or Y-axis is possible as well.

It is possible that the microarray receiving portion 10 is formed independent of the microarray receiving portion cluster 60. Accordingly, the microarray receiving portion 10 of the embodiment of FIG. 4 would in particular have a separate cover film 38.

FIG. 5 illustrates a sectional view of an embodiment of a microarray receiving portion 10, wherein the microarray receiving portion 10 substantially corresponds to the microarray receiving portion of FIG. 4 (independent of the microarray receiving portion cluster 60) along the section plane V.

Different from the embodiment in FIG. 4, FIG. 5 shows a bottom film 36. This bottom film 36 is connected with the carrier structure 16. This connection between the bottom film 36 and the carrier structure 16 is preferably an adhesive connection. It is particularly preferred that the bottom film 36 is designed to be peeled off or removed, so that a user can remove the bottom film 36 from the microarray receiving portion 10, in particular prior to application. As an alternative or in addition, it is possible that the bottom film 36 is designed such that it can be penetrated by the microarray 22, i.e., in particular the microneedles 24. In particular, the bottom film 36 may comprise an adhesive layer in particular on the lower side illustrated, so that the microarray receiving portion 10 can be adhesively connected with an application site through the adhesive layer of the bottom film 36.

In the form illustrated, the microarray receiving portion 10 is in an undeflected or non-applied position. The microarray receiving portion flexure hinge 26, which in particular is a linear plate-shaped flexure hinge, is thus not deflected. A convexly shaped force induction structure 34 is connected to the rear side of the microarray 22 or the rear side of the carrier surface 20. This convex force induction structure 34 makes it possible, in particular upon the application of force by means of an oppositely convex applicator, that the application of the microarray 22 is effected along the normal vector to the application site, i.e., in particular to the skin. Thus, a deflection along the Z-axis is effected thereby, and an optimal puncturing and application of the microneedles into the skin is possible.

The microneedle 22 is protected from the environment by the bottom film 36 and the cover film 38 and/or the carrier surface 20. Here, in particular a sterile protection from the environment is possible.

Figure 6:
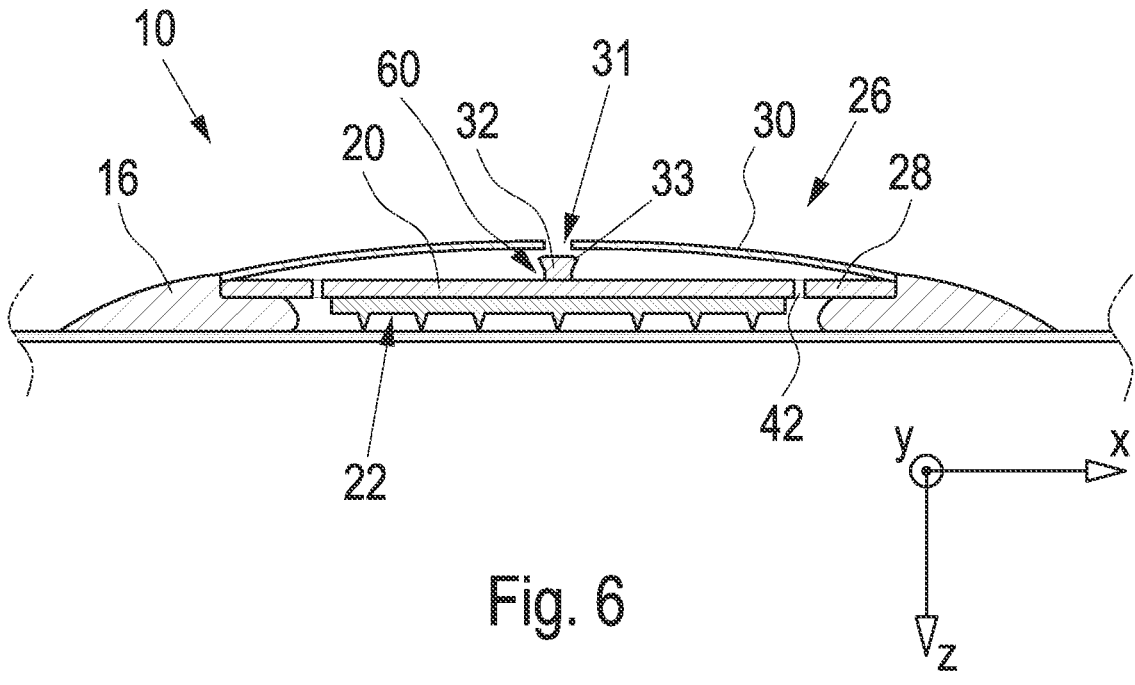
FIG. 6 is a schematic sectional view of a further embodiment of a microarray receiving portion.

FIG. 6 illustrates a further embodiment of a microarray receiving portion 10. The embodiment of FIG. 6 corresponds largely to the embodiment of FIG. 5. In contrast to the embodiment of FIG. 5, the microarray receiving portion of FIG. 6 has no force induction structure 34. Further, the embodiment of FIG. 6 is illustrated without a cover film 38. However, it is also possible to provide a cover film 38 in the embodiment of FIG. 6.

In addition, the embodiment of the microarray receiving portion hinge device 26 of FIG. 6 differs from the embodiment of FIG. 5. Here, the microarray receiving portion hinge device 26 comprises a first microarray receiving portion flexure hinge 28, which microarray receiving portion flexure hinge 28 essentially corresponds to the embodiment of FIG. 5, i.e., it is configured in particular as a linear plate-shaped flexure hinge. In addition, the microarray receiving portion comprises a second microarray receiving portion flexure hinge 30 above the first microarray receiving portion flexure hinge 28. The second microarray receiving portion flexure hinge 30 preferably is a plate, in particular of spring steel, which plate is bent upward and thus is in a prestressed state. In other words: the design of the second microarray receiving portion flexure hinge 30 corresponds to the design of a "clicker". When pressure is applied on the second microarray receiving portion flexure hinge 30 from above, the same is deformed and jumps to the opposite side, whereupon the second microarray receiving portion hinge device hinge 30 bends downward and remains in this position. Due to this deformation jump, the second microarray receiving portion flexure hinge 30 acts on the first microarray receiving portion flexure hinge 28 and deflects the same as well. Thereby, a deflection or application of the microarray 22 connected with the first microarray receiving portion flexure hinge 28.

In the embodiment illustrated the microarray receiving portion 10 comprises a blocking device configured as a latching device 60. As illustrated, the latching device 60 comprises a pin 32, as well as an opening 31 of the second flexure hinge 30. The pin 32 is connected, in particular formed integrally with the first microarray receiving portion flexure hinge 28. Preferably, the pin 32 has a structure of approximately half a bone, so that a kind of hemisphere or thickening 33 is provided at one end. The pin 32 tapers towards the other side connected with the first microarray receiving portion flexure hinge 28. When the second microarray receiving portion flexure hinge 30 is deflected, the second microarray receiving portion flexure hinge 30 puts itself over the thickening 33 of the in particular flexible pin 32 by a an opening 31 provided therein. Thereby, the second microarray receiving portion flexure hinge 30 is latched with the first microarray receiving portion flexure hinge 28, so that subsequent relative movement between the microarray receiving portion flexure hinges 28, 30 are prevented. In other words: the second microarray receiving portion flexure hinge 30 is latched with the first microarray receiving portion flexure hinge 28. Due to the prestressing of the second microarray receiving portion flexure hinge 30, the first microarray receiving portion flexure hinge 28 and the second microarray receiving portion flexure hinge 30 remain in the deflected position so that the microarray 22 is maintained in a deflected and, thus, applied state.

Instead of the embodiment illustrated having the latching device 60, a design of the microarray receiving portion 10 without the latching device and, accordingly, also without the opening 31 of the second microarray receiving portion flexure hinge 30 is also possible.

Due to the two microarray receiving portion flexure hinges 28, 30, which are arranged in parallel to each other, no tilting, i.e., no movement of the microarray 22 around the X- and/or Y-axis is possible, in particular in contrast to the embodiment of FIG. 5. The two microarray receiving portion flexure hinges 28, 30 thus arranged with respect to each other ensure that only a deflection along the Z-axis is possible.

Figure 7:
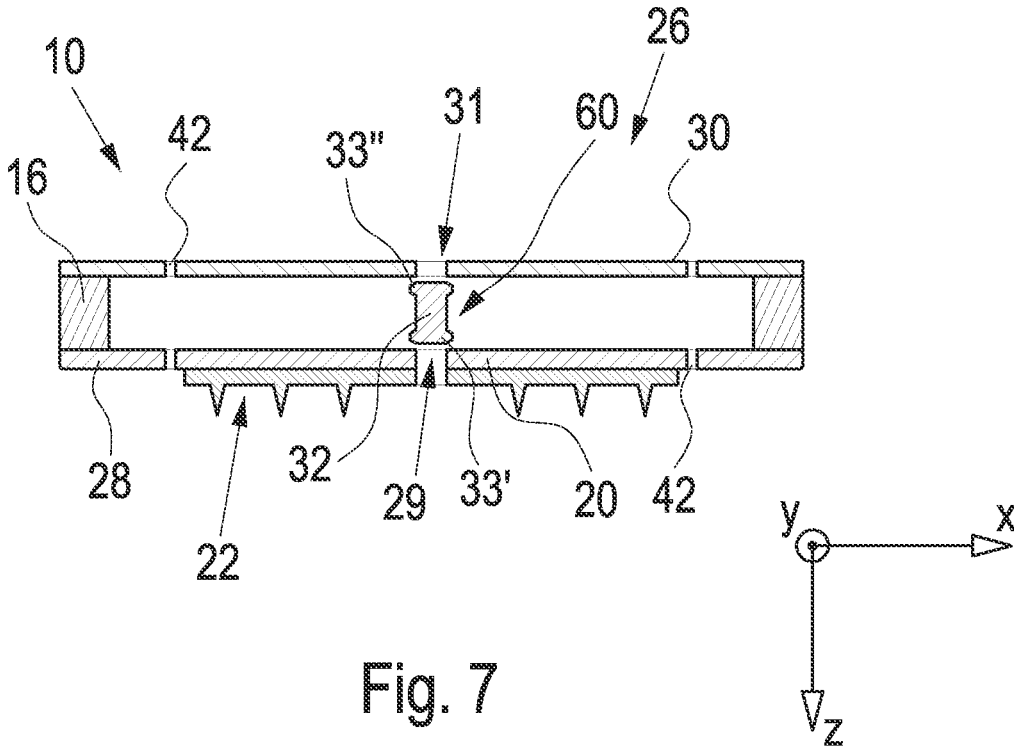
FIG. 7 is a schematic sectional view of a further embodiment of a microarray receiving portion.

FIG. 7 illustrates another embodiment of a microarray receiving portion 10. The microarray receiving portion 10 comprises two microarray receiving portion flexure hinges 28, 30. Here, both microarray receiving portion flexure hinges 28, 30 are designed similar to the microarray receiving portion flexure hinge 28 of FIG. 5, i.e., in particular as linear plate-shaped flexure hinges. Again, the composition of the microarray receiving portion flexure hinges 28, 30 ensures that only a deflection along the Z-axis is possible. The first microarray receiving portion flexure hinge 28 has an opening 29 and the second microarray receiving portion flexure hinge 30 has an opening 31. A latching device 60 is provided between the openings, which is designed as a latching pin 32 in the embodiment illustrated. The latching pin 32 essentially has the shape of a bone, so that thickenings 33', 33'' are located at both ends of the latching pin 32. When the second microarray receiving portion flexure hinge 30 is deflected in the positive Z-direction, also the first microarray receiving portion flexure hinge 28 is deflected due to the action of the second microarray receiving portion flexure hinge 30 on the first microarray receiving portion flexure hinge 28, and the microarray 22 is thereby applied in the Z-direction. In addition, this deflection ensures that the first microarray receiving portion flexure hinge 28, as well as the microarray receiving portion flexure hinge 30 are put over the latching pin 32 by their openings 29, 31 and remain latched in the central portion of the latching pin 32. In this manner, the first microarray receiving portion flexure hinge 28 is latched with respect to the second microarray receiving portion flexure hinge 30.

A carrier structure 16 is provided between the first microarray receiving portion flexure hinge 28 and the second microarray receiving portion flexure hinge 30. Similar to the embodiment of FIG. 5, this carrier structure 16 can also extend below the first microarray receiving portion flexure hinge 28 and thereby in particular create a spacing from the application site. In addition, similar to the embodiment of FIG. 5, it is also possible to provide a bottom film 36 and/or a cover film 38 and/or a force application structure 34 in the embodiment of FIG. 7.

Figures 8A, 8B:
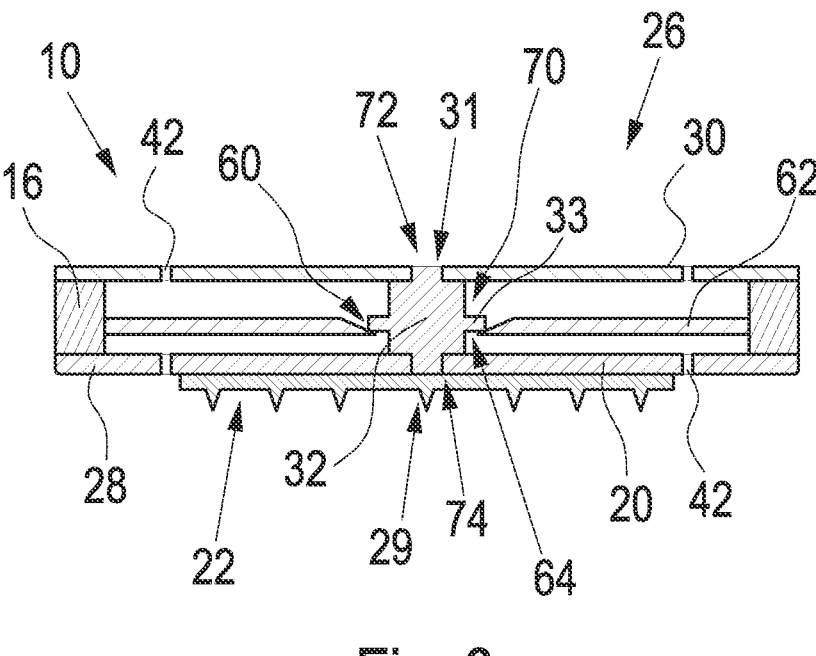
FIG. 8a is a schematic sectional view of a further embodiment of a microarray receiving portion according to the present disclosure.
FIG. 8b is a schematic sectional view of a further embodiment of a microarray receiving portion of FIG. 8a in an applied position.
Figure 9:
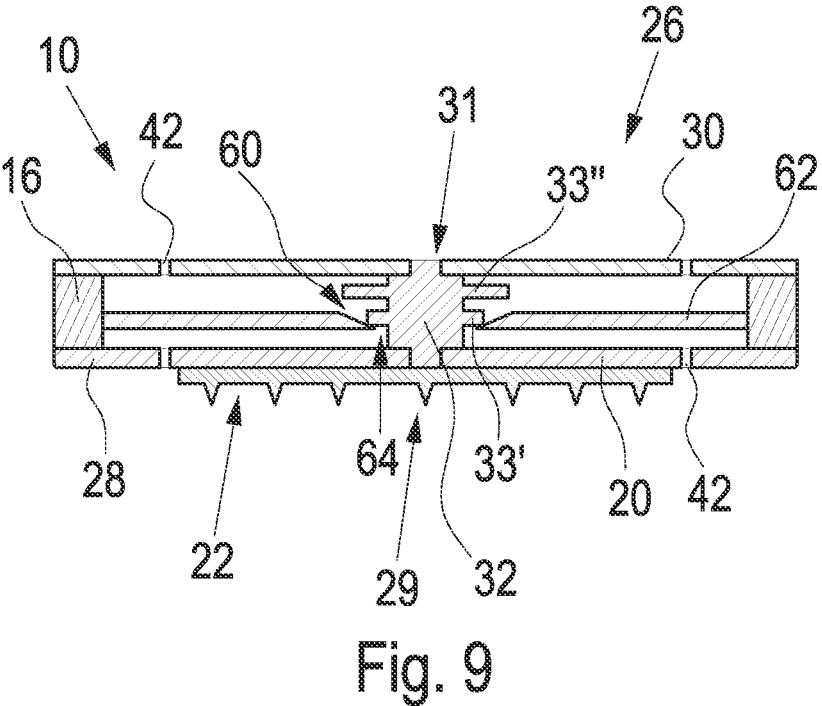
FIG. 9 is a schematic sectional view of a further embodiment of a microarray receiving portion according to the present disclosure.

FIG. 8a illustrates a further embodiment of a microarray receiving portion 10 according to the disclosure. The embodiment is based on the embodiment of FIG. 7.

In contrast to the embodiment of FIG. 7, the pin 32 is inserted into the openings 29, 31 already in the initial state. Here, the pin 32 corresponds essentially to the design of a shaft with two shaft shoulders 72, 74, while various shapes of the pin 32 are possible, such as round, rectangular, square etc. The shaft shoulder 72 is inserted into the opening 31, while the shaft shoulder 74 is inserted into the opening 29. Here, the pin 32 acts as a spacer between the first flexure hinge 28 and the second flexure hinge 30, Moreover, the embodiment comprises a guide device 70 that includes the shaft shoulders 72, 74 of the pin 32, as well as the openings 29, 31. Here, the pin 32, acting as a kind of guide rod, ensures a linear guiding of the first flexure hinge 28 and the second flexure hinge 30, so that only a deflection along the Z-direction is possible. If the first flexure hinge 28 were acted upon such that it would be tilted or experience a moment, the pin 32 absorbs this moment and prevents tilting. As a consequence, there only is a linear deflection of the microarray 22 along the Z-direction.

The embodiment also comprises a latching device 60. The latching device 60 includes the protrusion 33 of the pin 32, as well as the latching plate 62. As illustrated, the latching plate 62 is immovably connected, in particular integrally formed with the carrier structure 16 and comprises an opening 64 with a chamfer. In the initial position (FIG. 8a), the protrusion 33, which may also be configured as a bead, rests at the opening 64 of the latching plate 62. When the second flexure hinge 30 is deflected along the Z-direction, e.g., due to a user pressing ion the same, a transmission of force occurs through the pin 32 onto the first flexure hinge 28 and, therefore, also a deflection of the pin 32 and the first flexure hinge 28 in the Z-direction occurs. In the process, the protrusion 33 overcomes the opening 64 of the latching plate 62. As a consequence, the pin 32 latches below the latching plate 62 (in the Z-direction). Thereby, the first flexure hinge 28 is fixed in the deflected position, whereby a kind of holding pressure is exerted on the microarray 22 connected with the first flexure hinge 28. Thus, it is possible to maintain the microarray 22 in an applied state.

It is possible that the second flexure hinge 30 returns to the initial position after an initial deflection. This may be achieved in particular by providing the plug-in connection between the shaft shoulder 72 and the opening 31 as a releasable connection. On the other hand, it is possible that the shaft shoulder 72 and the opening 31 and/or the shaft shoulder 74 and the opening 29 are inseparable, in particular integral. It is also possible that the pin 32 has no shaft shoulders 72, 74 and/or the flexure hinges 28, 30 have no openings 29, 31, but the pin 32 is connected on one side directly with the first flexure hinge 28 and, on the other side, with the second flexure hinge 30, preferably in an inseparable manner, in particular integrally.

The protrusion 33 may be flexible. As an alternative or in addition, the latching plate 62 or the area of the opening 64 of the latching plate 62 can be flexible.

An embodiment similar to the embodiment of FIG. 8a is also possible which has no latching device 60, i.e., in particular no latching plate 62 and/or no protrusion 33 on the pin 32.

The invention claimed is:

1. An applicator comprising:
   a microarray, the microarray having a convex receiving portion;
   a cylindrical housing;
   a plunger for the acceleration of the microarray, the plunger being movable inside the housing, the plunger having a first side and a second side opposite the first side;
   a hinge device for movability of the plunger relative to the cylindrical housing;
   a target force trigger, the target force trigger fixing the plunger relative to the cylindrical housing and releasing the plunger for movement relative to the cylindrical housing when at least a target force is applied;
   an actuation surface for the application of the target force, the actuation surface being connected with the first side of the plunger; and
   a convex structure connected with the second side of the plunger for transmitting a punctual force to the microarray to be applied and configured to directly contact over the convex receiving portion, the convex structure oriented opposite the actuation surface.

2. The applicator according to claim 1, wherein the actuation surface is accessible from outside the applicator.

3. The applicator according to claim 1, further comprising a spring sheet that indirectly or directly prestresses the plunger to create a prestress which moves the plunger after a movement release.

4. The applicator according to claim 1, wherein the plunger is rigid.

5. The applicator according to claim 1, wherein the target force trigger comprises a rated breaking point and/or a fit, the rated breaking point and/or the fit being between the housing and the plunger.

6. The applicator according to claim 5, wherein the fit comprises a bead and/or a groove.

7. The applicator according to claim 1, wherein the hinge device is a flexure hinge device.

8. The applicator according to claim 1, wherein the hinge device comprises a sliding joint or a helical joint or a revolute joint or a ball joint.

9. The applicator according to claim 1, comprising a retaining device for the fixation of the plunger after a movement release.

10. The applicator according to claim 9, wherein the retaining device is a latching device.

11. The applicator according to claim 1, wherein the plunger is configured to be connected directly or indirectly with the microarray.

12. The applicator according to claim 1, further comprising a connection device for the connection of the applicator with a microarray receiving portion and/or an application site.

13. The applicator according to claim 12, wherein the connection device comprises a thread and/or a plug-in connector and/or a form-fitting connection element and/or a flange and/or an adhesive connection device and/or a lug and/or a loop.

14. An application system for the application of a microarray, comprising:

the applicator according to claim 1; and a microarray receiving portion cluster connected with the microarray receiving portion, wherein the microarray receiving portion being is arranged relative to the applicator and/or being is connected with the applicator such that the plunger applies the microarray.

15. The application system according to claim 14, wherein the microarray receiving portion comprises:

a first side;

a second side;

a carrier structure for the connection of the microarray receiving portion with an application site;

a carrier surface connected with the carrier structure;

the microarray connected with the carrier surface; and a microarray receiving portion hinge device between the carrier surface and the carrier structure, wherein the microarray receiving portion hinge device allows for a movement of the microarray connected with the carrier surface along the extension of the microarray relative to the carrier structure.

16. The application system according to claim 15, comprising a force application structure connected with a rear side of the carrier surface, the plunger of the applicator acting indirectly or directly on the force application structure.

17. The application system according to claim 16, wherein the force application structure extends convexly from the rear side of the carrier surface.

* * * * *